United States Patent [19]

Ogura et al.

[11] 4,425,805
[45] Jan. 17, 1984

[54] RESPIRATION FLOWMETER

[75] Inventors: Ichiro Ogura; Ayao Itoh, both of Yokohama, Japan

[73] Assignee: Tokyo Shibaura Denki Kabushiki Kaisha, Kawasaki, Japan

[21] Appl. No.: 316,286

[22] Filed: Oct. 29, 1981

[30] Foreign Application Priority Data

Oct. 31, 1980 [JP] Japan .................. 55-153261

[51] Int. Cl.³ .......................... G01F 1/66; A61B 5/08
[52] U.S. Cl. .................. 73/861.29; 128/725; 364/510
[58] Field of Search ............ 73/861.29; 128/725; 364/510, 565

[56] References Cited

U.S. PATENT DOCUMENTS

| | | | |
|---|---|---|---|
| 3,237,453 | 3/1966 | Yamamoto et al. | 73/861.28 |
| 3,329,017 | 7/1967 | Yamamoto et al. | 73/861.28 |
| 3,402,606 | 9/1968 | Bruha | 73/861.29 |
| 3,918,304 | 11/1975 | Abruzzo et al. | 73/861.29 |
| 3,922,525 | 11/1975 | Kozak et al. | 250/231 R |
| 4,052,896 | 10/1977 | Lee et al. | 73/861.29 |
| 4,095,457 | 6/1978 | Koda et al. | 73/53 |
| 4,312,238 | 1/1982 | Rey | 73/861.29 X |

FOREIGN PATENT DOCUMENTS 553456 7/1977 U.S.S.R. .................. 73/861.29

OTHER PUBLICATIONS

Telemetry of Respiratory Air Flow, Kimmich et al., Conference; International Symposium of Biotelemetry, pp. 5-8, May 1971.
IEEE Transaction on Instrumentation and Measurement; vol. IM-28, No. 4; Jean Appel, Alain Bruere, Francois Dunand; Dec. 1979.
IEEE Trans. on BME-27 No. 10, Oct. 1980 (Plaut et al.), pp. 549-558.
HP Journal (Blais et al.), vol. 30, No. 9, Sep. 1979, pp. 20-24.

Primary Examiner—Charles A. Ruehl
Assistant Examiner—Tom Noland
Attorney, Agent, or Firm—Oblon, Fisher, Spivak, McClelland & Maier

[57] ABSTRACT

At a pair of recesses formed on an inner wall of a conduit along a line slanted with respect to the flow direction of a respiration gas flowing through the measuring conduit, a pair of ultrasonic transducers are provided with their ultrasonic transmitting and receiving surfaces oppositely facing each other along the above line. A propagating time T1 from the time when one of said ultrasonic transducers is driven to produce ultrasonic wave until the other transducer receives the ultrasonic wave, and a propagating time difference ΔT are measured. A digital processor calculates a flow velocity of the respiration gas using the measured values in accordance with the following equation $$V = \frac{-2(2d + L)^2}{L\cos\theta} \cdot \frac{\Delta T}{T_a^2}$$

where d is a distance between the pair of transducers free from an effect by the flow velocity of the gas; L a distance influenced by the flow velocity of the same; θ an angle of the direction of the respiration flow with respect to a line coupling the pair of transducers; ΔT the propagating time difference; and Ta a value obtained by substituting the propagating time difference ΔT from the double (2 T1) of the ultrasonic propagating time T1.

7 Claims, 5 Drawing Figures

RESPIRATION FLOWMETER

BACKGROUND OF THE INVENTION

The present invention relates to a respiration flowmeter, which makes use of ultrasonic waves.

Recently, there has been recognized the necessity of monitoring a respiration function of a patient, inter alia a postoperative serious case. To effect this, it is essential to continuously monitor a flow velocity or flow rate of the respiration, as its basic approach. A first and important requirement for the inspiration flowmeter used for such end is not to inflict a physical and mental load on the patient. Particularly, the respiration flowmeter structured to give a difficulty in breathing, is improper. Conventional flowmeters such as differential-pressure type flowmeters, hot-wire type flowmeters or turbine type flowmeters have been used as respiration flowmeters, but, in measuring the respiration at a low flow velocity of a newborn, for example, the respiration flowmeters of these types work unstably or more adversely cannot measure the respiration flow rate. Generally, on the other hand, when comparing the expiration with the inspiration, there are great differences in temperature, humidity and gas composition. Therefore, even in case of the respiration flowmeter using the ultrasonic wave, a measuring error arising from a change of an ultrasonic propagating velocity in the respiration gas under measurement is not negligible. Thus, the conventional respiration flowmeters have been unsuccessful in providing perfect solutions to the above problems.

SUMMARY OF THE INVENTION

Accordingly, an object of the present invention is to provide a respiration flowmeter which can measure a respiration with a high precision and for a short response time, without inflicting a pain or load on patients.

To achieve the above object, there is provided a respiration flowmeter comprising: a conduit through which expiration and inspiration flow; a pair of recesses formed along a line slanted with respect to a flow direction of the respiration gas; a pair of ultrasonic transducers provided in the recesses with their ultrasonic transmitting and receiving surfaces oppositely faced each other along the line; means simultaneously switching the ultrasonic transducers between a drive mode and a receiving mode; digital counting means for measuring either of the two propagating times taken for ultrasonic wave radiated from one of the pair of driven transducers to reach the other tansducer and a difference between the two propagating times; means for judging the flow direction of the respiration gas; means for generating a signal for requesting calculation of a flow velocity of the respiration gas every time the pair of transducers are driven; means for storing the flow direction, the propagation times and the propagation time difference in response to the calculation request signal; and means for calculating and storing a flow rate of the respiration gas on the basis of the stored values.

BRIEF DESCRIPTION OF THE DRAWINGS

FIG. 3 shows timing diagrams of signals at the respective portions of the embodiment shown in FIG. 2.

DETAILED DESCRIPTION OF THE PREFERRED EMBODIMENT

Figure 1:
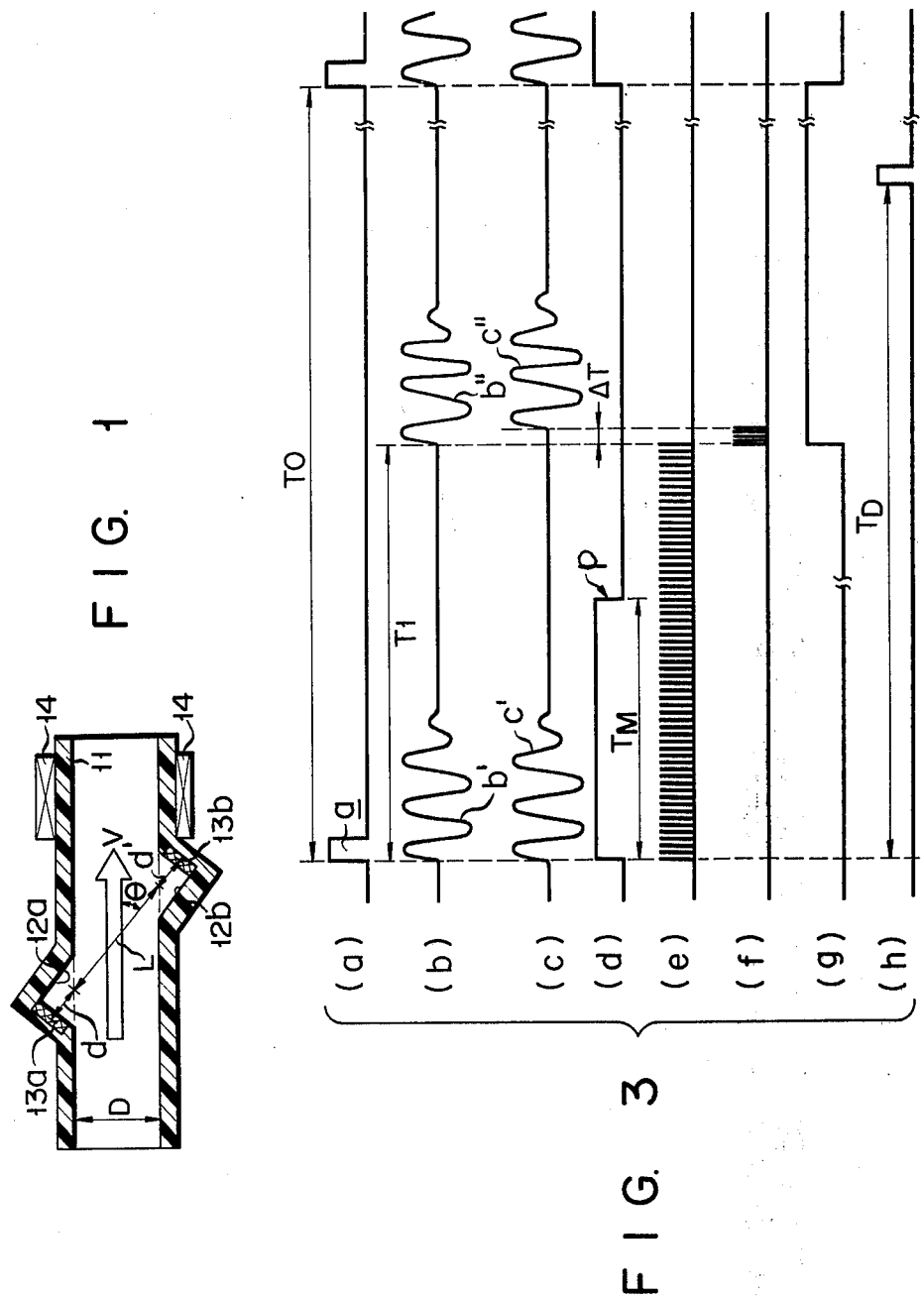
FIG. 1 shows a cross sectional view of a conduit provided with a pair of ultrasonic transducers used in an embodiment of a respiration flowmeter according to the present invention.

A structure of a conduit provided with a pair of ultrasonic transducers used in an embodiment of a respiration flowmeter according to the present invention will first be described referring to FIG. 1. In the figure, an expiration gas, for example, flows through a conduit 11, which is made of polycarbonate, for example, and has an inner diameter D, along its axis and at a flow velocity V in the direction of an arrow. The conduit 11 may also be made of metal or plastic. Accordingly, the inspiration gas flows at a flow velocity V' in the opposite direction to that of the arrow. A pair of recesses 12a and 12b are provided on the inner wall of the conduit 11 along a line slanted at a center of the respiration gas flow, for example, with respect to the gas flow. A pair of ultrasonic transducers 13a and 13b are respectively provided on the inner wall of the recesses 12a and 12b, facing at their transmitting and receiving surfaces each other along the slant line. Lead wires (not shown) for leading drive signals to the ultrasonic transducers 13a and 13b and ultrasonic signals received from the ultrasonic transducers 13a and 13b may be connected through the walls of the recesses 12a and 12b to the transducers 13a and 13b from the rear sides of the transducers, respectively. This structure allows the respiration gas to smoothly flow through the conduit 11 without being interrupted by the pair of transducers 13a and 13b. It is evident that, with this structure, a propagating velocity of the ultrasonic wave propagating portions d and d' within the recesses 12a and 12b are not influenced by a flow velocity of the respiration gas. Accordingly, a distance over which the propagating velocity is influenced by the flow velocity of the gas between the transducers 13a and 3b is L. If it is assumed that an angle of the direction V of the respiration gas flow with respect to the propagating direction of the ultrasonic wave is $\theta$ and a sonic velocity in the respiration gas is C, a propagating time T1 of the ultrasonic pulses radiated from the transducer 13a to the transducer 13b in the respiration flow direction V is given by $$T1 = \frac{2d}{C} + \frac{L}{C + V\cos\theta} \quad (\because d = d') \quad (1)$$

An opposite propagating time T2 of the ultrasonic pulses radiated from the transducer 13b to 13a is $$T2 = \frac{2d}{C} + \frac{L}{C - V\cos\theta} \quad (\because d = d') \quad (2)$$

A difference time $\Delta T$ between the propagating times T1 and T2 is $$\Delta T = T1 - T2 = \frac{-2LV\cos\theta}{C^2 - V^2\cos^2\theta} \approx \frac{-2LV\cos\theta}{C^2} \quad (3)$$

$$(\because V << C)$$

Rearranging the equation (3) with respect to the flow velocity V, we have $$V = \frac{-C^2}{2L\cos\theta} \Delta T \quad (4)$$

The sonic velocity C changes depending on temperature, humidity and gas composition of the respiration air. Accordingly, if the flow velocity of the respiration is measured by merely using the ultrasonic propagating time difference $\Delta T$, the measured value is infuenced by the above factors.

Let us calculate the sonic velocity C by using the sum Ta of the two ultrasonic propagating times T1 and T2. Then, $$Ta = T1 + T2 = 2T1 - \Delta T = \frac{4d}{C} + \frac{2CL}{C^2 - V^2\cos^2\theta} \approx \frac{2(2d + L)}{C} \quad (5)$$

$$(V < < C)$$

Rearranging the equation (5) with respect to the sonic velocity C, we obtain $$C = \frac{2(2d + L)}{Ta} = \frac{2(2d + L)}{2T1 - \Delta T} \quad (6)$$

Substituting the equation (6) into the equation (4), then we have $$V = \frac{-2(2d + L)^2}{L\cos\theta} \cdot \frac{\Delta T}{Ta^2} = \frac{-2(2d + L)^2}{L\cos\theta} \cdot \frac{\Delta T}{(2T1 - \Delta T)^2} \quad (7)$$

The equation (7) implies that the flow velocity V can be measured by measuring only the ultrasonic propagating time difference $\Delta T$ and the ultrasonic propagating time T1, independently of the sonic velocity C, that is, without directly accounting for effects by temperature, humidity and gas composition.

In the structure shown in FIG. 1, an electric heater 14 is mounted around the conduit 11 and/or the transducers 13a and 13b, if necessary, in order to prevent the condensation made when the expiration of 100% humidity flows through the conduit 11.

Figure 2:
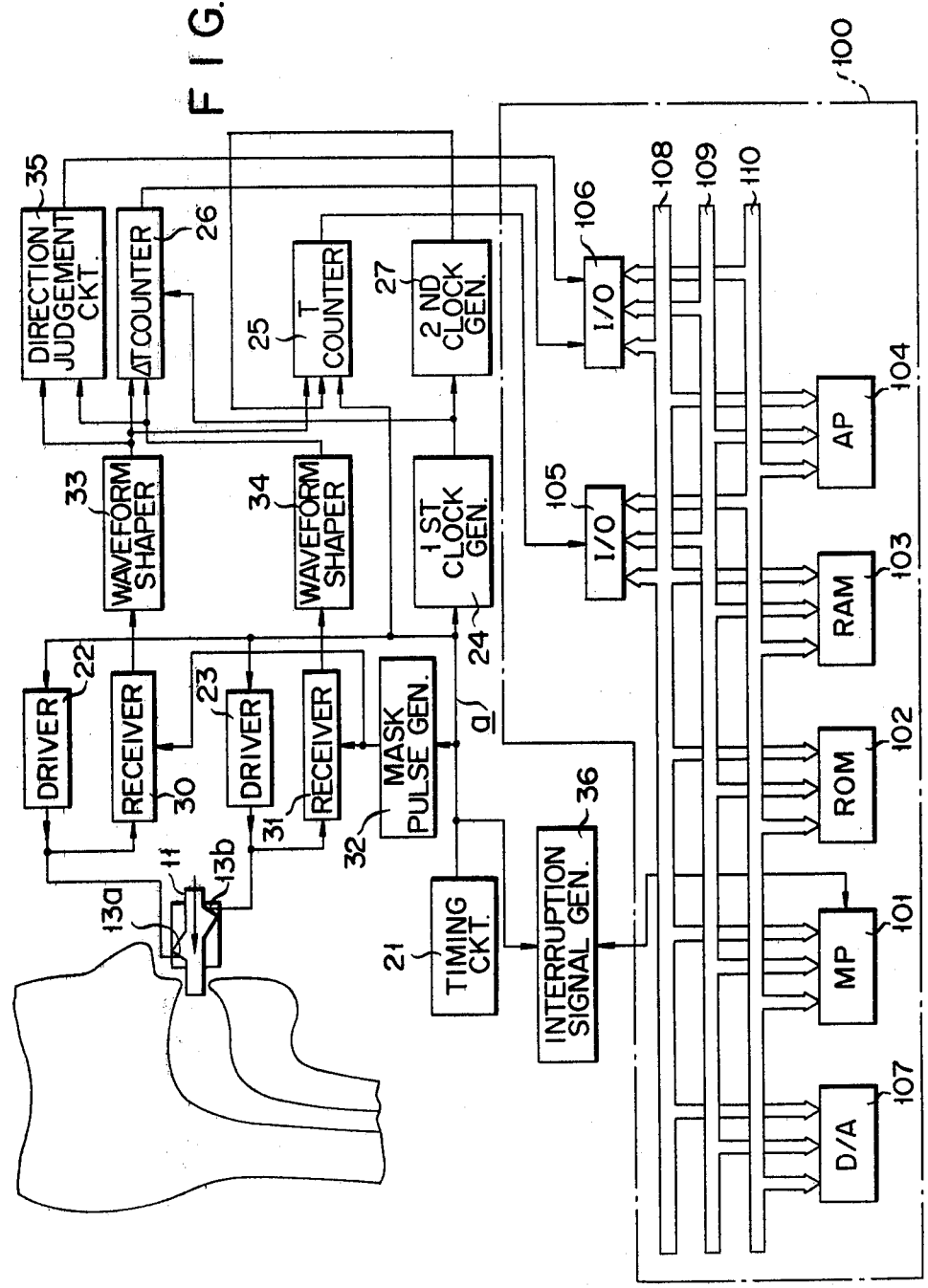
FIG. 2 is a block diagram illustrating an overall arrangement of the embodiment used together with the conduit shown in FIG. 1.

An arrangement of an embodiment of the present invention will be described referring to a block diagram of a device shown in FIG. 2 and signal waveforms shown in FIG. 3. In FIG. 2, a pulse a (FIG. 3(a)) produced from a timing circuit 21 for each time T0 is applied to driving circuits 22 and 23, a first clock generating circuit 24 and a T counter 25. The time T0 designates a time in the order of several msec to 10 msec. The first clock generating circuit 24 generates clock signals at 100 MHz, for example, for transfer to a $\Delta T$ counter 26 for counting the ultrasonic propagating time difference $\Delta T$ (0 to several $\mu$sec). The T counter 25 counts a propagating time T1, and starts to count in response to the pulse a. The clock signal used for counting the propagating time T1 is supplied from a second clock generating circuit 27. The second clock generating circuit 27 is driven by an output signal from the first clock generating circuit 24, and produces second clock signals at 10 MHz, which is, for example, 1/10 that of the first clock signals.

Upon receipt of the pulse a, the driving circuits 22 and 23 generate signals b' and c' (FIGS. 3(b) and 3(c)) for driving ultrasonic transducers 13a and 13b. Ultrasonic waves simultaneously radiated from the ultrasonic transducers 13a and 13b travel toward the opposite side ultrasonic transducers 13b and 13a, and velocity of the waves is changed on the way by the flow velocity of the respiration gas flowing through the conduit 11. The ultrasonic waves transmitted are received by the corresponding transducers 13a and 13b and are transformed into electrical signals b'' and c'' which are in turn applied to the receivers 30 and 31, respectively. Receivers 30 and 31, which are controlled by an output of a mask pulse generating circuit 32, reject signals applied during a period $T_M$ after the ultrasonic transducers 13a and 13b are driven (FIG. 3(d)). Accordingly, the receivers 30 and 31 discriminate signals b' and c' (FIGS. 3(b) and 3(c)) for driving the ultrasonic transducers 13a and 13b from received signals b'' and c'', and receive only the received signals b'' and c''. The mask pulse generating circuit 32 is also driven by the output pulses from the timing circuit 21 and produces p(FIG. 3(d)). The output signals from the receivers 30 and 31 are respectively applied to waveform shapers 33 and 34 where those are waveform-shaped, and those waveform-shaped ones are applied to a direction judgment circuit 35, the $\Delta T$ counter 26, and the T counter 25.

The T counter 25 receives the output signal from the waveform shaper 33 to terminate its counting which has been performed under drive of the timing circuit 21. The T counter 25 counts a time taken for an ultrasonic wave to travel from the ultrasonic wave transducer 13a to the transducer 13b (FIG. 3(e)). In the present embodiment, an inspiration condition is illustrated as shown in FIG. 2 in which a patient 10 breathes in the direction of an arrow. Under this condition, the signal b'' goes ahead the signal c'', as shown in FIG. 3. In an expiration condition that the patient 10 breathes out, the signal c'' goes ahead the signal b''.

The $\Delta T$ counter 26 starts its counting responsive to the leading signal of those output signals from the waveform shapers 33 and 34, that is, the output signal from the waveform shaper 33 in this case, and stops its counting responsive to the lagged signal, that is, the output signal from the waveform shaper 34. In this way, the counter 26 counts the ultrasonic propagating time difference $\Delta T$, as shown in FIG. 3(f).

The direction judging circuit 35 also receives output signals from the waveform shapers 33 and 34. The circuit 35 judges that the respiration is the inspiration when the output signal from the waveform shaper 33 leads ahead the output signal derived from the waveform shaper 34. On the other hand, it judges that the respiration is the expiration when the former lags behind the latter. At this judgment, its output goes high (see FIG. 3(g)) or low in level. The direction judging circuit 35 may be formed of a general flip-flop with a clear terminal.

At the time that the three data necessary for measuring the flow velocity, i.e. the direction of the respiration, the ultrasonic propagating time T1 and the ultrasonic propagating time difference $\Delta T$, are measured, an interruption signal which is the output pulse a derived from the timing circuit 21 delayed by time $T_D$, 1 msec, for example, is applied from an interruption signal generating circuit 36 (see FIG. 3(h)). The interruption signal is a signal for driving an arithmetic circuit 100 so as to cause it to calculate a flow velocity by using the above three data.

The arithmetic circuit 100 is comprised of a microprocessor (MP) 101, a read only memory (ROM) 102 for storing a program executed by the arithmetic circuit 100 and constants, a random access memory (RAM) 103 for storing the data produced during, before or after the execution of the program, an arithmetic processor (AP) 104 for executing the operations such as numerical operation, and ports (I/O) 105 and 106 for inputting the three data, and a digital to analog (D/A) converter 107 for producing a calculated flow velocity in the form of an analog signal. Those components are interconnected by a control bus 108, an address bus 109 and a data bus 110.

Figure 4:
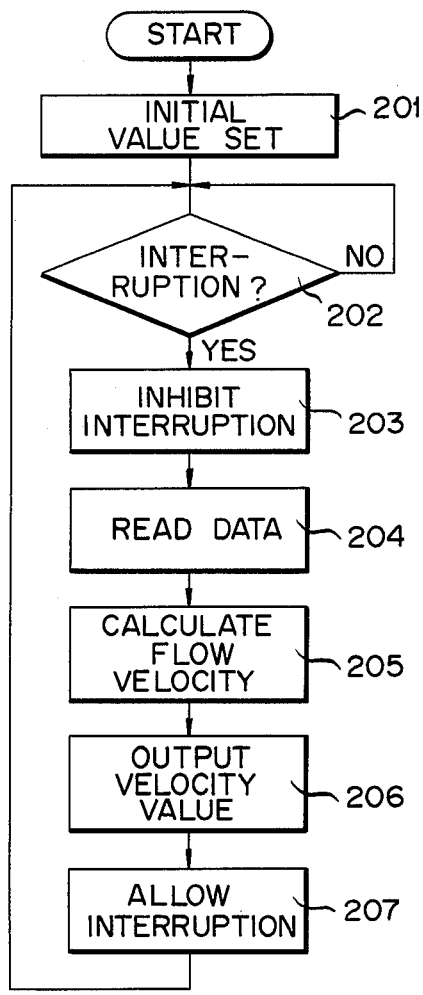
FIGS. 4 and 5 illustrate flow charts useful in explaining the operation of the embodiment shown in FIG. 2.

The arithmetic circuit 100 proceeds with the operation in accordance with a flow chart shown in FIG. 4.

In a step 201, following the power on, initial values are set in the microprocessor 101, the ports 105 and 106 for inputting data, the memory 102 and the like in the arithmetic circuit 100. Then, in a step 202, the arithmetic circuit 100 is in a standby mode for waiting the interruption signal. When the interruption pulse enters the microprocessor 101, the microprocessor 101 sets itself to be in an interruption inhibiting mode, in a step 203. In the next step 204, the microprocessor 101 fetches the data of the direction of the gas flow, the ultrasonic propagating time difference $\Delta T$, and the ultrasonic propagating time T1 from the ports 105 and 106 for the data inputting, arranges the data into a format easy to be processed. The data are then stored in the RAM 102. For ease of explanation, the $\Delta T$ will be treated as data with a sign representing a direction of the gas flow. Then, in a step 205, the microprocessor 101 executes a flow velocity of the gas in accordance with a flow chart shown in FIG. 5 by using the data in the step 204. The resultant data of flow velocity is delivered from D/A converter 107 through the step 206. Finally, in a step 207, the microprocessor 101 sets itself to be in an interruption permission mode and waits an interruption signal produced in the next transmission and reception of the ultrasonic wave. Through the repetition of the above-mentioned operation, the respiration flowmeter of the present embodiment can measure at a rate of about 100 times per second, a flow velocity and a direction of the pulsating gas flow which instantaneously change with the respiration.

Figure 5:
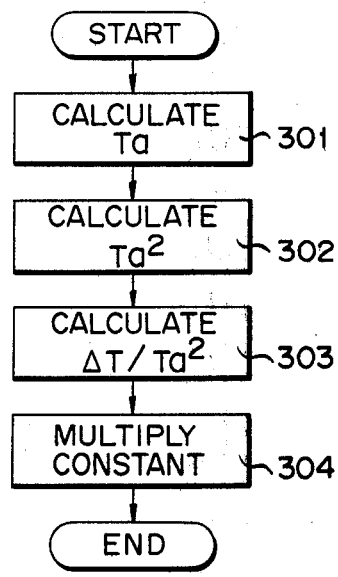

The flow chart shown in FIG. 5 illustrating a process flow of the calculation of the flow velocity according to the equation (7) will be given hereinafter.

In a step 301, the ultrasonic propagating time T1 and the ultrasonic propagating time difference $\Delta T$ stored in the RAM 103 are set in the arithmetic processor (AP) 104 where the ultrasonic propagating time sum TA ($=2T1-\Delta T$) is obtained. The $\Delta T$ used when the Ta is calculated has a sign representing the flow direction, as described above, and a direction of the inspiration flow is represented by a negative sign in the present embodiment.

In a step 302, an instruction for squaring the ultrasonic propagating time sum Ta is transferred to the AP 104 where $Ta^2$ is calculated. In the next step 303, the $\Delta T$ data is read out from the RAM 103 and set in the AP 104 where the ratio $\Delta T/Ta^2$ is calculated. Finally, in a step 304, the constant in the equation (7), $$\frac{-2(2d+L)^2}{L\cos\theta},$$

is read out from the ROM 102 and is similarly set in the AP 104. Then, the MP 101 transfers an instruction to multiply the constant in the equation (7) by the ratio $\Delta T/Ta^2$ to the AP 104 where the flow rate is calculated. During the course of the operation, the data transmission between the ROM (102), the RAM (103) or the ports I/O 105 and 106 for data inputting and the microprocessor MP 101 is performed in a usual way. For example, the ROM 102 is designated through the address bus 109; a control signal for data read or data write is transferred to the ROM 102 through the control bus 108; the data to be read or written is transferred through the data bus 110.

As described above, the present invention successfully solves the problems of the prior art as previously stated and provides an almost ideal respiration flowmeter. It should be noted that, in the respiration flowmeter according to the present invention, the signal processing for the measurement is digitally performed, not through the D/A converting process, in the almost entire circuit portions except the ultrasonic transmitting and receiving portions. This feature eliminates the temperature drift which is problematic in the low flow rate measurement. Additionally, there is no need of the fine circuit adjustment essential to the analog circuit. This feature makes easy the manufacture of the flowmeter. Further, the analog to digital converter connected to the data processing is of course unnecessary, leading to simplification of the circuit construction, cost reduction and high reliability of the operation.

Further, the respiration flowmeter of the present invention, which measures the flow velocity of the respiration by using the ultrasonic propagating time and the ultrasonic propagating time difference, allows the frequency of the clock signal to be selected for securing a measuring accuracy required for a measurement to be made. Therefore, the circuit construction is simple and an unnecessary high speed circuit is omitted. Further, the values thus measured are arranged in a minimum data length, so that the succeeding data process may be effectively performed.

In the above-mentioned embodiment, the receiver circuits 30 and 31 are so connected to be supplied with the mask pulse for discriminate signals b' and c' for driving ultrasonic transducers 13a and 13b from received signals b'' and c''. The waveform shapers 33 and 34 may also be connected to be controlled by the mask pulse.

What is claimed is:

1. A respiration flowmeter comprising:
    a conduit through which expiration and inspiration flow;
    a pair of recesses formed on an inner wall of the conduit along a line slanted with respect to a flow direction of the respiration gas;
    a pair of ultrasonic transducers provided in said recesses with their ultrasonic transmitting and receiving surfaces oppositely faced each other along said line;
    means simultaneously switching said ultrasonic transducers between a drive mode and a receiving mode;
    digital counting means for measuring either of the two propagating times taken for ultrasonic wave radiated from one of said pair of driven transducers to reach the other transducer and a difference between said two propagating times;

means for judging the flow direction of said respiration gas;

means for generating a signal for requesting calculation of a flow velocity of the respiration gas every time said pair of transducers are driven;

means for storing said flow direction, said two propagation times and said propagation time difference in response to said calculation request signal; and means for calculating and storing a flow rate of said respiration gas on the basis of said stored values.

2. A respiration flowmeter according to claim 1, wherein an electric heater for preventing condensation is provided on the periphery of said conduit and around the ultrasonic transducers.

3. A respiration flowmeter according to claim 1, wherein said switching means include a circuit which supplies a mask pulse for preventing receiving circuits or waveform shapers from receiving signals when drive circuits are driven.

4. A respiration flowmeter according to claim 1, wherein said means for calculating and storing said flow rate of respiration gas include an arithmetic processor for obtaining a flow velocity V by executing the following operation $$V = \frac{-2(2d + L)^2}{L\cos\theta} \cdot \frac{\Delta T}{Ta^2}$$

where d is a distance between said pair of transducers free from an effect by the flow velocity of said gas; L a distance influenced by the flow velocity of the same; $\theta$ an angle of the direction of the respiration flow with respect to a line coupling said pair of transducers; $\Delta T$ the propagating time difference; and Ta a value obtained by subtracting said propagating time difference $\Delta T$ from the double of the ultrasonic propagating time T1.

5. A respiration flowmeter according to claim 1, wherein said digital counting means for measuring either of two propagating times and propagating time difference are composed of a first clock means generating a first clock, a second clock means generating a second clock, a first clock counting means for measuring the propagating time difference by counting the first clock and a second clock counting means for mesuring the propagating times by counting the second clock, the second clock having a frequency lower than that of the first clock.

6. A respiration flowmeter according to claim 1, wherein an electric heater for preventing condensation is provided on the periphery of said conduit.

7. A respiration flowmeter according to claim 1, wherein an electric heater for preventing condensation is provided around the ultrasonic transducers.

* * * * *